United States Patent [19]

Bowers-Daines et al.

[11] Patent Number: 5,252,745

[45] Date of Patent: Oct. 12, 1993

[54] PREPARATION AND USE OF IODOPROPARGYL ESTERS OF α-AMINO ACID DERIVATIVES AS ANTIMICROBIAL AGENTS

[75] Inventors: Margaret M. Bowers-Daines, Blue Bell; Barry C. Lange, Lansdale, both of Pa.

[73] Assignee: Rohm and Haas Company, Philadelphia, Pa.

[21] Appl. No.: 704,906

[22] Filed: May 21, 1991

Related U.S. Application Data

[63] Continuation of Ser. No. 398,867, Aug. 25, 1989, abandoned.

[51] Int. Cl.⁵ ............................................. C07C 229/00
[52] U.S. Cl. ..................................... 548/479; 554/62; 560/16; 560/29; 560/32; 560/33; 560/39; 560/41; 560/148; 560/153; 560/157; 560/159; 560/155; 560/160; 560/163; 560/169; 560/170; 560/172
[58] Field of Search .................. 560/16, 24, 29, 39, 560/41, 147, 148, 153, 155, 157, 159, 160, 169, 170, 32, 33, 163, 172; 260/404; 548/479; 554/62

[56] References Cited

U.S. PATENT DOCUMENTS

| | | |
|---|---|---|
| 4,151,299 | 4/1979 | Hubele . |
| 4,206,228 | 6/1980 | Hubele . |
| 4,294,850 | 10/1981 | Hubele . |
| 4,427,696 | 1/1984 | Hubele . |
| 4,439,447 | 3/1984 | Hubele . |
| 4,535,088 | 8/1985 | Makisumi et al. . |
| 4,639,541 | 1/1987 | Staiger ................... 560/20 |

FOREIGN PATENT DOCUMENTS

| | | | |
|---|---|---|---|
| 14032 | 8/1980 | European Pat. Off. ............ | 560/167 |
| 125614 | 9/1979 | Japan . | |
| 1500581 | 2/1978 | United Kingdom . | |

OTHER PUBLICATIONS

"Hackh's Chemical Dictionary," 4th Ed. pp. 27 and 92 (1969).
"Peptides:Synthesis, Structure and Function", Proc. Am. Pept. Symposium, 7th (1981) pp. 101-104.
Green, T., "Protective Groups in Organic Synthesis", J. Wiley & Sons, Inc., N.Y. (1981), pp. 218-287.
"Bulletin of Chemical Society of Japan", Ando T., Shioi S., Nakagawa, M. (1972) 45,2611.

Primary Examiner—Michael L. Shippen
Attorney, Agent, or Firm—Michael B. Fein

[57] ABSTRACT

Antimicrobial compounds of the formula

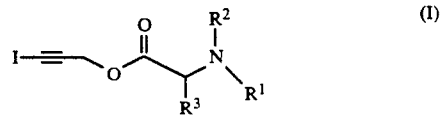

(I)

wherein $R^1$ is selected from the group consisting of H, an amine protective group, and a moiety of the formula

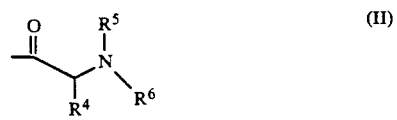

(II)

wherein
$R^2$, $R^5$, and $R^6$ are independently selected from H and an amine protective group;
$R^3$ and $R^4$ are independently selected from H, lower alkyl, aryl, arylalkyl, $CH_2OR$, $CH_2SR$ or $CH(CH_3)OR$;
$R = H$, propargyl lower alkyl, arylalkyl or aryl;
wherein $R^1$ and $R^2$ or $R^5$ and $R^6$ can be joined to form a ring; and wherein when $R^1$ and $R^2$ or $R^5$ and $R^6$ are both H, the compound is either in free base form or in salt form.

3 Claims, No Drawings

PREPARATION AND USE OF IODOPROPARGYL ESTERS OF α-AMINO ACID DERIVATIVES AS ANTIMICROBIAL AGENTS

This application is a continuation of Ser. No. 07/398,867 filed Aug. 25, 1989, and now abandoned.

BACKGROUND OF THE INVENTION

1. Field of the Invention

This invention relates to the field of antimicrobial agents.

2. Description of the Prior Art

Ger. Offen. DE 2515091 (1975), Ciba Geigy AG, discloses microbiocidal anilides which are acylanilides which have an amino acid moiety and an iodopropargyl fragment as shown, but the point of attachment of the iodopropargyl fragment is not directly on the amino acid portion of the molecule. These compounds are N-iodopropargyloxy acid amides.

Kokai Tokkyo Koho JP 54/125614 (1979), Shigaken Pharmaceutical Co., Ltd. discloses antimicrobial iodopropargyloxy acid amide derivatives useful for bactericides and agricultural fungicides.

U.S. Pat. No. 4,535,088-A (1985) assigned to Shionogi and Co., shows 2-(3-iodo)propargyl-amino-thiazole derivatives as useful as antimicrobials, i.e. antibacterial and antifungal agents.

*Peptides: Synthesis, Structure and Function; Proc. Am. Pept. Symposium,* 7th, (1981), pp 101–4 describes the synthesis of C-iodopropargyl glycine. There is no mention of antibacterial or antifungal activity.

SUMMARY OF THE INVENTION

Many of the antimicrobials of the prior art have toxicity and/or environmental problems.

It is an object of the present invention to provide novel antimicrobial compounds which have improved toxicity profiles and are not harmful to the environment.

These objects, and others which will become apparent from the following disclosure, are achieved by the present invention which comprises in one aspect compounds of the formula

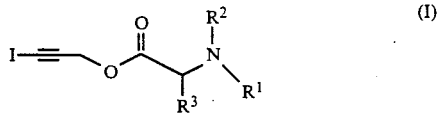

wherein $R^1$ can be H, an amine protective group, or

$R^2$, $R^5$, and $R^6$ are independently selected from H and an amine protective group;

$R^3$ and $R^4$ are independently selected from H, lower alkyl, aryl, arylalkyl, $CH_2OR$, $CH_2SR$ or $CH(CH_3)OR$;

R=H, propargyl lower alkyl, arylalkyl or aryl;

wherein $R^1$ and $R^2$ can be joined to form a ring: and wherein when $R^1$ and $R^2$ or $R^5$ and $R^6$ are both H, the compound is either in free base form or in salt form.

Another aspect of the invention is when said amine protective group is selected from amides, carbamates, imines, enamines, aminoacetals, N-alkyl, N-benzyl, N-sulfenyl or N-sulfonyl.

A further aspect of the invention are the compounds in salt form.

DETAILED DESCRIPTION OF THE INVENTION AND THE PREFERRED EMBODIMENTS

The compounds of the invention have been discovered to be unexpectedly effective antimicrobials. The compounds are designed to biodegrade down to non-toxic amino acid components.

The compounds of the invention can have $R^1$ as an amine protective group. Suitable amine protective groups are amides, carbamates, imines, enamines, aminoacetals, N-alkyl, N-benzyl, N-sulfenyl or N-sulfonyl, and the like. For detailed examples of the suitable amine protective groups, see Greene, T.; "Protective Groups in Organic Synthesis," John Wiley & Sons, Inc., New York, (1981), pages 218-87.

When $R^1$ and $R^2$ are H, or when $R^1$ is structure II and both $R^5$ and $R^6$ are H, the compound can be in either free base or salt form. Suitable conjugate acids to form the salts are either organic or inorganic acids, for example hydrochloric acid, sulfuric acid, acetic acid, propionic acid, sorbic acid, trifluoroacetic acid, hydrobromic acid, formic acid, and the like.

When $R^1$ and $R^2$ or $R^5$ and $R^6$ are joined to form a ring, suitable rings are cyclic imide derivatives such as phthaloyl, diphenylmaleoyl, dithiasuccinoyl, and the like.

When $R^3$, $R^4$ and R are lower alkyl imides, i.e., phthalimido, diphenylmaleimido, dithiasuccinimido, said alkyl can have 1 to 8, preferably 1 to 4 carbon atoms and can be substituted. When $R^3$, $R^4$ or R are aryl, suitable aryls are phenyl, sustituted phenyl, and the like.

When $R^3$, $R^4$ or R are arylalkyl, suitable moities are benzyl, diphenylmethyl, sustituted benzyl, and the like.

Some representative compounds include the following:

1. N-t-butoxycarbonylglycine iodopropargyl ester
2. N-t-butoxycarbonyl-L-alanine iodopropargyl ester
3. N-t-butoxycarbonyl-O-benzyl-L-serine iodopropargyl ester
4. N-t-butoxycarbonyl-S-benzyl-L-cysteine iodopropargyl ester
5. N-t-butoxycarbonyl-O-benzyl-L-threonine iodopropargyl ester
6. N-t-butoxycarbonyl-S-propargyl-L-cysteine iodopropargyl ester
7. glycine iodopropargyl ester trifluoroacetate
8. L-alanine iodopropargyl ester trifluoroacetate
9. O-benzyl-L-serine iodopropargyl ester trifluoroacetate
10. S-benzyl-L-cysteine iodopropargyl ester trifluoroacetate
11. O-benzyl-L-threonine iodopropargyl ester trifluoroacetate
12. N-t-butoxycarbonyl-L-alanylglycine iodopropargyl ester
13. N-t-butoxycarbonyl-L-alanyl-L-alanine iodopropargyl ester
14. N-t-butoxycarbonyl-L-alanyl-O-benzyl-L-serine iodopropargyl ester
15. N-t-butoxycarbonyl-L-alanyl-S-benzyl-L-cysteine iodopropargyl ester 16. N-t-butoxycarbonyl-L-alanyl-O-benzyl-L-threonine iodopropargyl ester
17. L-alanylglycine iodopropargyl ester trifluoroacetate
18. L-alanyl-L-alanine iodopropargyl ester trifluoroacetate
19. L-alanyl-O-benzyl-L-serine iodopropargyl ester trifluoroacetate
20. L-alanyl-S-benzyl-L-cysteine iodopropargyl ester trifluoroacetate
21. L-alanyl-O-benzyl-L-threonine iodopropargyl ester trifluoroacetate
22. L-alanine iodopropargyl ester
23. N-t-butoxycarbonyl-D-alanine iodopropargyl ester
24. D-alanine iodopropargyl ester trifuoroacetate
25. N-t-butoxycarbonyl-D-alanyl-D-alanine iodopropargyl ester
26. N-t-butoxycarbonyl-D-alanyl-L-alanine iodopropargyl ester
27. N-t-butoxycarbonylglycyl-L-alanine iodopropargyl ester
28. N-acetylglycine iodopropargyl ester
29. N-benzoylglycine iodopropargyl ester
30. N-phthaloylglycine iodopropargyl ester
31. N-benzyloxycarbonylglycine iodopropargyl ester
32. N-formylglycine iodopropargyl ester
33. N-propionylglycine iodopropargyl ester
34. N-octanoylglycine iodopropargyl ester
35. N-2,4-hexadienoylglycine iodopropargyl ester a solution or suspension of the n-protected D- or L-amino acid in anhydrous solvents such as dichloromethane, 1,4-dioxane, tetrahydrofuran, dimethoxyethane, toluene or N,N-dimethylformamide is allowed to react with iodopropargyl alcohol in the presence of 4-dimethylaminopyridine and 1-(3-dimethylaminopropyl)-3-ethylcarbodiimide hydrochloride. The reaction time usually takes place within a range of 1 to 18 hours. The reaction is usually conducted between 0° and 25° C.

Numerous other peptide synthesis coupling reagents may be used as esterification agents. Alternatively, the D- or L-amino acid may be converted to an acid chloride or to an activated ester and then reacted with iodopropargyl alcohol to form the desired ester. Such coupling and activation procedures are discussed in the next "Principles of Peptide Synthesis", Bodanszky, M.; Springer-Verlag: New York, N.Y., (1984).

Iodopropargyl alcohol can be prepared by the procedure described in Bulletin of the Chemical Society of Japan, Ando, T., Shioi, S., Nakagawa, M., (1972), 45, 2611.

The n-protected D- or L- amino acid where $R^1=(CH_3)_3COCO$, $PhCH_2OCO, CH_3CO, PhCO, HCO, R^2=H$ and $R^1, R^2=$phthaloyl are commercially available.

The n-protected D- or L- amino acid where $R^1=CH_3CH_2CO$, $H(CH_2)_7CO$, and $R^2, R^3=H$ can be prepared via N-acylation of commercially available glycine methyl ester hydrochloride with the corresponding acid chloride in the presence of a base such as 4-dimethylaminopyridine or triethylamine in an appropriate anhydrous solvent such as dichloromethane.

TABLE I

STRUCTURES and melting points of the representative compounds

| Compound No | $R^1$ | $R^2$ | $R^6$ | $R^4$ | $R^5$ | $R^3$ | Melting Point (°C.) |
|---|---|---|---|---|---|---|---|
| 1 | $(CH_3)_3COCO$ | H | | | | H | 65-68 |
| 2 | $(CH_3)_3COCO$ | H | | | | $CH_3$ | 71-73 |
| 3 | $(CH_3)_3COCO$ | H | | | | $CH_2OCH_2Ph$ | oil |
| 4 | $(CH_3)_3COCO$ | H | | | | $CH_2SCH_2Ph$ | 84-86.5 |
| 5 | $(CH_3)_3COCO$ | H | | | | $CH(CH_3)OCH_2Ph$ | oil |
| 6 | $(CH_3)_3COCO$ | H | | | | $CH_2SCH_2CCl$ | oil |
| 7 | H (trifluoroacetate salt) | H | | | | H | 130-131 |
| 8 | H (trifluoroacetate salt) | H | | | | $CH_3$ | oil |
| 9 | H (trifluoroacetate salt) | H | | | | $CH_2OCH_2Ph$ | — |
| 10 | H (trifluoroacetate salt) | H | | | | $CH_2SCH_2Ph$ | — |
| 11 | H (trifluoroacetate salt) | H | | | | $CH(CH_3)OCH_2Ph$ | oil |
| 12 | $COCHR^4NR^5R^6$ | H | $(CH_3)_3COCO$ | $CH_3$ | H | H | amorph. solid |
| 13 | $COCHR^4NR^5R^6$ | H | $(CH_3)_3COCO$ | $CH_3$ | H | $CH_3$ | amorph. solid |
| 14 | $COCHR^4NR^5R^6$ | H | $(CH_3)_3COCO$ | $CH_3$ | H | $CH_2OCH_2Ph$ | amorph. solid |
| 15 | $COCHR^4NR^5R^6$ | H | $(CH_3)_3COCO$ | $CH_3$ | H | $CH_2SCH_2Ph$ | amorp. solid |
| 16 | $COCHR^4NR^5R^6$ | H | $(CH_3)_3COCO$ | $CH_3$ | H | $CH(CH_3)OCH_2Ph$ | amorph. solid |
| 17 | $COCHR^4NR^5R^6$ | H | H (trifluoroacetate salt) | $CH_3$ | H | H | oil |
| 18 | $COCHR^4NR^5R^6$ | H | H (trifluoroacetate salt) | $CH_3$ | H | $CH_3$ | oil |
| 19 | $COCHR^4NR^5R^6$ | H | H (trifluoroacetate salt) | $CH_3$ | H | $CH_2OCH_2Ph$ | amorp. solid |
| 20 | $COCHR^4NR^5R^6$ | H | H (trifluoroacetate salt) | $CH_3$ | H | $CH_2SCH_2Ph$ | amorp. solid |
| 21 | $COCHR^4NR^5R^6$ | H | H (trifluoroacetate salt) | $CH_3$ | H | $CH(CH_3)OCH_2Ph$ | oil |
| 22 | H | H | | | | $CH_3$ | — |
| 23 | $(CH_3)_3COCO$ | H | | | | $CH_3$ | — |
| 24 | H (trifluoroacetate salt) | H | | | | $CH_3$ | oil |
| 25 | $COCHR^4NR^5R^6$ | H | $(CH_3)_3COCO$ | $CH_3$ | H | $CH_3$ | amorp. solid |
| 26 | $COCHR^4NR^5R^6$ | H | $(CH_3)_3COCO$ | $CH_3$ | H | $CH_3$ | amorp. solid |
| 27 | $COCHR^4NR^5R^6$ | H | $(CH_3)_3COCO$ | H | H | $CH_3$ | amorp. solid |
| 28 | $CH_3CO$ | H | | | | H | 119-121.5 |
| 29 | PhCO | H | | | | H | 116-120 |
| 30 | | -phthaloyl- | | | | H | 155 |
| 31 | $PhCH_2OCO$ | H | | | | H | 73-75 |
| 32 | HCO | H | | | | H | 81-85 |
| 33 | $CH_3CH_2CO$ | H | | | | H | — |
| 34 | $H(CH_2)_7CO$ | H | | | | H | 87-89 |
| 35 | 2,4-sorboyl | H | | | | H | 137-138.5 |

The compounds of the invention wherein $R^1$ is H or an amine protective group can be prepared by esterification of the appropriately n-protected D- or L-amino acid with iodopropargyl alcohol.

A variety of esterification methods may be utilized to prepare the compounds of the invention. For example, The n-protected D- or L- amino acid where $R^1$=sorbyl and $R^2$, $R^3$=H can be prepared via N-acylation of glycine methyl ester hydrochloride with sorbic acid in the presence of a base (triethylamine or 4-dimethylaminopyridine) and a peptide coupling reagent (dicyclohexylcarbodiimide or 1-(3-dimethylaminopropyl)-3-ethylcarbodiimide hydrochloride) in an appropriate anhydrous solvent (dichloromethane or 1,4-dioxane). The resultant N-acylated glycine methyl ester can be hydrolyzed to the N-protected D- or L- amino acid with lithium hydroxide or sodium hydroxide in aqueous tetrahydrofuran followed by acidification with an aqueous inorganic acid such as potassium hydrogen sulfate or hydrochloric acid.

Compound numbers 7-11, and 24, which are in the form of trifluoroacetate salts where $R^1$, $R^2$=H, $R^3$=H, $CH_3$, $CH_2OCH_2Ph$, $CH_2SCH_2Ph$, $CH(CH_3)OCH_2Ph$ can be prepared from the corresponding N-tert-butoxycarbonyl iodopropargyl ester (compound numbers 1-5, 23) by treatment with trifluoroacetic acid in dichloromethane.

Dipeptide compounds wherein $R^1$ is II can be synthesized as follows: A previously prepared iodopropargyl ester amine trifluoroacetate salt (compound numbers 7-11, 24) can be coupled with readily available N-tert-butoxycarbonyl protected D- or L- amino acids utilizing the various known peptide coupling methods described above. More specifically, to a solution or suspension of iodopropargyl ester amine trifluoroacetate salt (I) in anhydrous solvents such as dichloromethane, 1,4-dioxane, tetrahydrofuran, N,N-dimethylformamide, dimethoxyethane or toluene at a temperature between 0° and 25° C. under inert atmosphere is added a base such as triethylamine, N-methylmorpholine or 4-dimethylaminopyridine, followed by a readily available N-tert-butoxycarbonyl protected D- or L-amino acid, followed by N-hydroxybenzotriazole as a racemization suppression additive and catalyst, followed by the coupling agent such as dicyclohexycarbodiimide or 1-(3-dimethylaminopropyl)-3-ethylcarbodiimide hydrochloride. The reaction mixture is then stirred at a temperature between 0° and 25° C. for a time between 1 to 24 hours. The product N-tert-butoxycarbonyl dipeptide iodopropargyl ester is then isolated in the usual manner.

The trifluoroacetate salts of the dipeptides, (compound numbers 17-21) can be prepared from the corresponding N-t-butoxycarbonyl dipeptide iodopropargyl esters (II), (compound numbers 12-16) by treatment with trifluoroacetic acid in dichloromethane.

As stated above, compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungi, bacteria, algae, viruses and yeasts. The preferred utilities of the compositions are to protect wood, paint adhesive, glue, paper, textile, leather, plastics, cardboard, lubricants, cosmetics, food, caulking, feed and industrial cooling water from microorganisms.

The following lists specific industries and applications of the compounds or compositions:

| Industry | Application |
| --- | --- |
| Adhesives, sealants | adhesives |
| | caulks |
| | sealants |
| agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | Industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry rinse water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |

| Industry | Application |
|---|---|
| Paints and coatings coating | emulsions |
|  | paints |
| Paper and wood pulp, their products | absorbent materials of paper and wood pulp |
|  | packaging materials of paper and wood pulp |
|  | paper |
|  | paper products |
|  | paper treatment |
|  | soap wrap |
|  | wood pulp |
|  | wood pulp products |
| paper mill | paper mill slimicides |
|  | pulp and paper slurries |
| Petroleum refining, fuels | aviation fuels (jet fuel, aviation gas) |
|  | crude oils |
|  | burner, diesel and turbine fuel oils |
|  | coal slurries |
|  | diesel fuel additives |
|  | diesel fuels |
|  | fuels |
|  | gasoline |
|  | heating oils |
|  | hydrocarbons |
|  | kerosene |
|  | liquefied petroleum gas |
|  | petrochemical feedstocks |
|  | petroleum products, storage, transportation and production |
|  | recycled petroleum products |
|  | residual fuel oils |
|  | turbine oils |
| Photographic chemicals and process | photographic processing - wash water, rinses |
|  | photoprocessing |
|  | photoplate processing chemicals (developers, stabilizers etc) |
| Printing | fountain solutions (printing) |
|  | ink components (pigments, resins, solvents, etc) |
|  | inks |
| Sanitizers (active) | sanitizers |
|  | sanitizers-dairy |
|  | sanitizers-dental |
|  | sanitizers-fermentation |
|  | sanitizers-food preparation |
|  | sanitizers-food processing |
|  | sanitizers-medical |
|  | sanitizers-rendering |
|  | sanitizers-veterinary |
| Soaps, detergents, cleaners | cleaners |
|  | detergents |
|  | household cleaners |
|  | industrial cleaners |
|  | liquid soaps |
|  | oil and grease remover |
|  | powdered soaps |
|  | raw materials for cleaning products |
|  | soaps |
|  | surfactants |
| Textiles, textile products | bonded fabrics |
|  | burlap |
|  | canvas |
|  | canvas goods |
|  | carpet backing |
|  | carpets |
|  | clothing |
|  | coated fabrics |
|  | curtains |
|  | draperies |
|  | engineering textiles |
|  | fibers |
|  | geotextiles |
|  | goods made of textiles |
|  | knitted fabrics |
|  | nets |
|  | nonwoven fabrics |
|  | rope |
|  | rugs |
|  | textile accessories |
|  | textile products |
|  | textiles |
|  | upholstery |
|  | woven fabrics |
|  | yarn |
| Textile processing | dye fixatives |
|  | dyes |
|  | fiber lubricants |
|  | hand modifiers |
|  | sizes |
|  | textile processing fluids |
| Therapeutic (active or preservative) | animal health/veterinary |
|  | aquaculture |
|  | dental |
|  | human health |
|  | pharmaceutical/therapeutic |
| Water purification | charcoal beds |
|  | deionization resins |
|  | filters |
|  | membranes |
|  | reverse osmosis membranes |
|  | ultrafilters |
|  | water purification |
|  | water purification pipes, tubing |
| Wood applications | lazures (wood stains) |
|  | wood |
|  | wood products |
| Miscellaneous | alcohols |
|  | bedding incorporating water or gels |
|  | ceramic |
|  | contact lens cases-leaching |
|  | electronic circuitry |
|  | electronics chemicals |
|  | enzymes-food production |
|  | enzymes |
|  | enzymes-industrial |
|  | gel cushions |
|  | marine antifoulants |
|  | mildewcides |
|  | wood |
|  | plastics |
|  | laundry |
|  | mining |
|  | natural rubber latex |
|  | oil field injection waters including enhanced recover injection fluids, drilling, fracturing and completion fluids |
|  | pipes |
|  | plastics |
|  | polymer systems |
|  | polymers and resins (synthetic and natural |
|  | reagent preservation |
|  | rubber |
|  | rubber products |
|  | skin remover |
|  | solid protective/decorative films |
|  | stains |
|  | swimming pools |
|  | waste treatment |
|  | water beds |

The amounts of the compound to be used depend on the application. The useful amounts of a particular application are similar to amounts used for other microbiocide compounds.

The compound can be used in combination with other microbicides. The term "microbicide" is considered equivalent to "antimicrobial" as used herein.

Suitable methods of application of compounds of formula I to control fungi, bacteria, algae, viruses, yeasts, and the like are in amounts and with carriers, etc., as well known in the art.

The following examples are presented to illustrate a few embodiments of the invention, but are not to be considered as limiting.

EXAMPLE 1

N-t-Butoxycarbonylglycine iodopropargyl ester
(Compound #1)

To a magnetically stirred solution of N-t-butoxycarbonylglycine (3.00 g., 17.12 mmole) and iodopropargyl alcohol (3.12 g., 17.15 mmole) in anhydrous dichloromethane (40 ml.) cooled to 0° C. with an ice-bath was added 4-dimethylaminopyridine (0.21 g., 1.72 mmole) followed by 1-(3-dimethylaminopropyl)-3-ethylcarbodiimide hydrochloride (3.61 g., 18.83 mmole). After stirring at 0° C. for ½ hour, the reaction mixture was stored in a refrigerator at 6° C. overnight. The reaction mixture was transferred to a separatory funnel and diluted to 100 ml. with dichloromethane, then washed successively with water, 10% aqueous potassium hydrogen sulfate, water, saturated aqueous sodium bicarbonate, water and a final wash with saturated aqueous sodium chloride. The organic layer was dried with magnesium sulfate, filtered and concentrated in vacuo with a rotary evaporator to a clear colorless oil which crystallized on standing as N-t-butoxycarbonylglycine iodopropargyl ester (5.60 g., 96.4% yield). m.p.=65°-68° C. $^1$H-NMR (200 MHz, DMSO$_{d6}$)$\delta$=1.40 ppm, s, 9H; 3.73, d, 2H; 4.86, s, 2H; 7.28, t, 1H. IR (CDCl$_3$) 1165, 1505, 1715, 1760, 2205, 3460 cm$^{-1}$.

EXAMPLE 2

N-t-Butoxycarbonyl-L-alanine iodopropargyl ester
(Compound #2)

To a magnetically stirred solution of N-t-butoxycarbonyl-L-alanine (5.00 g., 0.026 mole) and iodopropargyl alcohol (4.81 g., 0.026 mole) in anhydrous dichloromethane (100 ml.) cooled to 0° C. with an ice-bath was added 4-dimethylaminopyridine (0.32 g., 0.0026 mole) followed by 1-(3-dimethylaminopropyl)-3-ethylcarbodiimide hydrochloride (5.57 g., 0.029 mole). The reaction mixture continued to stir at 0° C. for one hour, and was then stored in a refrigerator at 5° C. overnight. The reaction mixture was transferred to a separatory funnel and diluted to double volume (200 ml.) with dichloromethane, then washed successively with 100 ml. of water, 3×100 ml. of 10% aqueous potassium hydrogen sulfate, 100 ml. of water, 3×100 ml. of saturated aqueous sodium bicarbonate, 3×100 ml. of water and a final wash with 100 ml. of saturated aqueous sodium chloride. The organic layer was dried with magnesium sulfate, filtered and concentrated in vacuo with a rotary evaporator to a clear colorless oil which crystallized on standing. A quantitative yield (9.34 g.) of N-t-butoxycarbonyl-L-alanine iodopropargyl ester was obtained. m.p.=71°-73° C. $^1$H-NMR (200 MHz, DMSO$_{d6}$) $\delta$=1.25 ppm, d, 3H; 1.40, s, 9H; 4.01, m, 1H; 4.85, s, 2H; 7.33, d, 1H. IR (CHCl$_3$) 1170, 1375, 1400, 1715, 1750, 2205 cm$^{-1}$.

EXAMPLE 3

Glycine iodopropargyl ester trifluoroacetate
(Compound #7)

N-t-Butoxycarbonyl glycine iodopropargyl ester (Compound #1) (4.20 g., 12.39 mmole) was dissolved in anhydrous dichloromethane (20 ml.), cooled to 0° C. with an ice-bath, and treated with 10 ml. of trifluoroacetic acid. The reaction mixture was stirred magnetically at 0° C. for 1 hour and then allowed to warm to ambient temperature. The volatile solvents were removed under reduced pressure leaving a clear syrup which crystallized on standing to a white solid (4.20 g., 96% yield) as the desired trifluoroacetate salt product. m.p. 130°-131° C. $^1$H-NMR (200 MHz, DMSO$_{d6}$) $\delta$=3.92, s, 2H; 5.00, s; 2H; s; 9.1, broad m. IR (KBr) 1605, 1670, 1765, 2205, 2640 cm$^{-1}$.

EXAMPLE 4

L-Alanine iodopropargyl ester trifluoroacetate
(Compound #8)

N-t-Butoxycarbonyl-L-alanine iodopropargyl ester (Compound #2) (3.50 g., 9.91 mmole) was dissolved in anhydrous dichloromethane (20 ml.), cooled to 0° C. with an ice-bath, and treated with 10 ml. of trifluoroacetic acid. The reaction mixture was stirred magnetically at 0°-7° C. for 17 hours and then allowed to warm to ambient temperature. The volatile solvents were removed under reduced pressure leaving a clear colorless syrup as the desired trifluoroacetate salt product. $^1$H-NMR (200 MHz, D$_2$O) $\delta$=1.58 ppm, d, 3H;4.23, q, 1H; 4.99, s, 2H. IR (CHCl$_3$) 1175, 1675, 1765, 2230, 2250-3500 cm$^{-1}$.

EXAMPLE 5

N-t-Butoxycarbonyl-L-alanylglycine iodopropargyl ester (Compound #12)

To a magnetically stirred, anhydrous dichloromethane (20 ml.) solution of glycine iodopropargyl ester trifluoroacetate (Compound #7) (2.00 g., 5.66 mmole) held at 0° C. with an ice-bath was added triethylamine (0.79 ml., 5.67 mmole), followed by N-t-butoxycarbonyl-L-alanine (1.07 g., 5.66 mmole), 1-hydroxybenzotriazole hydrate (0.77 g., 5.70 mmole) and 1-(3-dimethylaminopropyl)-3-ethylcarbodiimide hydrochloride (1.30 g., 6.78 mmole). The reaction mixture was held at 5° C. for 17 hours. The resultant solution was transferred to a separatory funnel and diluted to an approximate volume of 100 ml. with dichloromethane, then washed successively with water, 10% aqueous potassium hydrogen sulfate, water, saturated aqueous sodium bicarbonate, water and a final wash with saturated aqueous sodium chloride. The organic layer was dried with magnesium sulfate, filtered and concentrated in vacuo with a rotary evaporator to give 2.09 g. (90% yield) of the desired N-t-butoxycarbonyl-L-alanylglycine iodopropargyl ester as a dry white foam. $^1$H-NMR (200 MHz, CDCl$_3$) $\delta$=1.40, d, 3H; 1.47, 1.77, two s, 9H; 4.08, d, 2H; 4.24, m, 1H; 4.90, s, 2H; 5.06, d, 1H; 6.81, s, 1H. IR (CHCl$_3$) 1160, 1375, 1495, 1690, 1755, 2200, 2985, 3440 cm$^{-1}$.

EXAMPLE 6

N-t-Butoxycarbonylglycl-L-alanine iodopropargyl ester (Compound #27)

To a magnetically stirred, anhydrous dichloromethane (30 ml.) solution of L-alanine iodopropargyl ester trifluoroacetate (Compound #8) (2.30 g., 6.27 mmole) held at 0° C. with an ice-bath was added triethylamine (0.96 ml., 6.89 mmole), followed by N-t-butoxycarbonylglycine (1.10 g., 6.28 mmole), 1-hydroxybenzotriazole hydrate (0.85 g., 6.29 mmole) and 1-(3-dimethylaminopropyl)-3-ethylcarbodiimide hydrochloride (1.56 g., 8.14 mmole). The reaction mixture was held at 0°-7° C. for 17 hours. The resultant solution was transferred to a separatory funnel and diluted to an approximate volume of 100 ml. with dichloromethane, then washed successively with 3×50 ml. of water, 3×50 ml. of 10% aqueous potassium hydrogen sulfate, 3×50 ml. of saturated aqueous sodium bicarbonate, 3×50 ml. of water and a final wash with 50 ml. of saturated aqueous sodium chloride. The organic layer was dried with magnesium sulfate, filtered and concentrated in vacuo with a rotary evaporator to give 1.80 g. (70% yield) of the desired N-t-butoxycarbonylglycyl-L-alanine iodopropargyl ester as a dry white foam. $^1$H-NMR (200 MHz, CDCl$_3$) $\delta$=1.45 ppm, d, 3H; 1.45, 1.72, two s, 9H; 3.82, d, 2H; 4.63, m, 1H; 4.87, s, 2H; 5.17, broad m, 1H; 6.67, d, 1H.

EXAMPLE 7

N-2,4-hexadienoylglycine iodopropargyl ester (Compound #35)

To a magnetically stirred mixture of glycine methyl ester hydrochloride (4.14 g., 32.97 mmole) and 4-dimethylaminopyridine (4.03 g., 32.99 mmole) in anhydrous dichloromethane (75 ml.) cooled to 0° C. with an ice-bath was added sorbic acid (3.36 g., 29.97 mmole), followed by 1-(3-dimethylaminopropyl)-3-ethylcarbodiimide hydrochloride (6.90 g., 35.99 mmole). The reaction mixture continued to stir at 0° C. for 20 minutes. After storing in a refrigerator at 5° C. overnight, the reaction mixture was transferred to a separatory funnel and diluted to double volume (150 ml.) with dichloromethane, then washed successively with 3×40 ml. of water, 3×40 ml. of 10% aqueous potassium hydrogen sulfate, 3×40 ml. of saturated aqueous sodium bicarbonate, 3×40 ml. of water and a final wash with 40 ml. of saturated aqueous sodium chloride. The organic layer was dried with magnesium sulfate, filtered and concentrated in vacuo with a rotary evaporator to a fluffy white solid. An 88% yield (4.84 g.) of N-sorboyl methyl ester was obtained. m.p.=121°-122° C. $^1$H-NMR (200 MHz, CDCl$_3$)$\delta$=1.84 ppm, t, 3H; 3.77, s, 3H; 3.77, s, 3H; 4.15, d, 2H; 5.83, d, 1H; 6.15, m, 3H; 7.24, m, 1H. IR (CHCl$_3$) 1010, 1380, 1445, 1525, 1625, 1645, 1675, 1750, 3000, 3440 cm$^{-1}$.

Sorboyl methyl ester (4.08 g., 22.27 mmole) was dissolved in 75 ml. of a tetrahydrofuran-water mixture (3:1) and treated with 0.602 g. (24.57 mmole) of lithium hydroxide. After magnetically stirring for three hours, the reaction mixture was concentrated under reduced pressure to a dry residue which was dissolved in a minimum amount of water. With magnetic stirring, this solution was acidified to a pH of 2 with 4.1 ml. (24.6 mmole) of 6N aqueous hydrochloric acid. The desired product sorboyl was isolated by filtration and dried in vacuo over P$_2$O$_5$ to afford 3.13 g. (83% yield). m.p.=164°-166° C. $^1$H-NMR (200 MHz, DMSO$_{d6}$)$\delta$=1.8 ppm, d, 3H; 3.85, d, 2H; 5.9-6.4, m, 3H; 7.03, dd, 1H; 8.32, t, 1H; 12.6, broad m, 1H.

To a magnetically stirred slurry of N-sorbylglycine (2.59 g., 15.31 mmole) and 4-dimethylaminopyridine (0.187 g., 1.53 mmole) in anhydrous dichloromethane (80 ml.) cooled to 0° C. with an ice-bath was added iodopropargyl alcohol (3.06 g., 16.82 mmole) followed by 1-(3-dimethylaminopropyl)-3-ethylcarbodiimide hydrochloride (4.11 g., 21.44 mmole). The reaction mixture continued to stir at 0° C. and slowly warm to ambient temperature as the ice melted. After stirring for 2.5 hours, the reaction mixture was stored in a refrigerator at 5° C. overnight. The reaction mixture was transferred to a separatory funnel and diluted to approximately 200 ml. with dichloromethane, then washed successively with 2×35 ml. of water, 2×35 ml. of 10% aqueous potassium hydrogen sulfate, 2×35 ml. of saturated aqueous sodium bicarbonate and a final wash with 50 ml. of saturated aqueous sodium chloride. The organic layer was dried with magnesium sulfate, filtered and concentrated in vacuo with a rotary evaporator to an orange solid (4.47 g.). This material was purified by flash column chromatography by dissolving it in dichloromethane and adsorbing it on to 14 g. of silica gel, then removing the solvent under reduced pressure. The resultant dry powder was applied on to the head of a 134 g. silica gel column and eluted with hexanes/ethyl acetate (2:1). Desired product N-sorbogl iodopropargyl ester was obtained as a crystalline solid in 40.4% yield after chromatography. m.p.=137°-138.5° C. $^1$H-NMR (200 MHz, CDCl$_3$)$\delta$=1.84 ppm, d, 3H; 4.18, d, 2H; 5.80, d, 1H; 5.95-6.30, m, 3H; 7.15-7.30, m, 1H.

EXAMPLE 8—BIOLOGICAL ACTIVITY

A. Biocidal Activity

Biocidal evaluations (bactericidal, algicidal, and fungicidal) were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm (or 100, 50, 25, 12.5, 6.2, 3.1, 1.6, and 0.8), respectively.

Each vessel is then inoculated with a cell suspension of the appropriate test organism. Bacteria are grown in broth, fungi on agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The algae culture contains green algae and blue-green bacteria, and is obtained from a cooling tower in Spring House, Penn. The algae culture is grown in Allen's medium on a rotary shaker under flourescent room lighting. This culture is further diluted with Allen's medium and then added to the test vessel.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA:
*Pseudomonas fluorescens* (PSFL), gram negative
*Pseudomonas aerugenosa* (PSAE), gram negative
*Escherichia coli* (ECOL), gram negative
*Staphylococcus aureus* (SAUR), gram positive
FUNGI:
*Aspergillus niger* (ANIG)
*Aureobasidium pullulans* (APUL)

The results of the minimum inhibitory concentration (MIC) tests of compounds of this invention are shown in Tables IIIa, IIIb, IIIc, V, VI, VII, and VIII against the microorganisms shown in Table IX.

B. In-Vitro Plant Fungicidal Tests

In-vitro tests of plant diseases were carried out. The organisms employed in the test are:
PYU *Pythium ultimum* (Oomycete)
PHY *Phytophthora capsici* (Oomycete)
PIR *Piricularia oryzae* (Ascomycete)
HEL *Cochliobolus sativus* (Ascomycete)
BOC *Botrytis cinerea* (Ascomycete)
FUS *Fusarium roseum* (Ascomycete)
SEP *Septoria nodorum* (Ascomycete)
RHI *Rhizoctonia solani* (Basidiomycete)
XAN *Xanthomonas campestris* (bacterium)

Methods:

1. Culture maintenance:

Transfers in steps 1 and 2 are done in a laminar flow hood. All 8 fungi and the bacterium used in this test are transferred and maintaned on potato dextrose agar plates each week (2 plates/organism). Organisms are used when they are the following ages: a. 1 week old: PYU, PHY, RHI; b. 2 weeks old: XAN, PIR, BOC, HEL, FUS, SEP, COL, MON, CER, UST, ALT; c. 3 weeks old: PSH, VEN. *Pythium ultimum* and *Phytophthora capsici* are transferred to asparagine-sucrose broth shake cultures (ASB). *Rhizoctonia solani, Fusarium roseum,* and *Xanthomonas campestris* are mainted in yeast extract-dextrose broth (YDB) on a shaker. Culture flasks are inoculated with 6 mycelial plugs each (except for Pythium which is inoculated with only 3 plugs) taken from PDA plates. All liquid shaker cultrues are used after 2 days growth.

2. Inoculum preparation.

Conidia and mycelium from PIR, BOC, HEL, SEP, COL, MON, CER, PSH, UST and ALT are lightly scraped off into YDB so that mostly conidia are used as inoculum. The conidial suspension is strained through a double layer of cheesecloth to remove mycelial clumps. One plate produces enough conidia or mycelium to inoculate 100 ml of YDB. XAN broth culture is poured (1 ml culture/100 ml broth) into YDB. PYU, PHY, RHI and FUS cultures are ground up (2-3 5 second bursts in a blender) and all but Pythium and Phytophthora are filtered through a dobule layer of sterile cheesecloth to remove large mycelial clumps. Ten ml of the culture solutions of *R. solani* and *F. roseum* are added to 90 ml of YSB and 10 ml of the *P. capsici* is added to 90 ml ASB. Two ml of the culture solution of *P. ultimum* is added to 98 ml of ASB. Care must be made not to overinoculate (e.g. solutions should appear fairly clear to the eye, yet when held up to light a faint cloudiness should be visible) or standards will not behave properly. The inoculum mixtures are placed in microtiter plates using a 12-tipped pipet. 175 $\mu$l (single dose) or 100 $\mu$l (dose-response test) of inoculum broth is placed in each well of the microtiter plates. The plates with inoculated media are placed in the refrigerator overnight. There are two replications per treatment.

3. Addition of compounds.

This operation is carried out in a hood. Six microtiter plates have 245 microliters of sterile water added to their wells ahead of time. 10 Mg a.i. (active ingredient) of the compounds are placed in 1 ml 1:1 acetone:methanol. 5 microliters of this solution is pipetted into the microtiter plates containing the sterile water according to the grid. There are 45 compounds and 3 control treatments per plate. There are 2 replicates per treatment. 25 Microliters of solution is transferred to the inoculated plates with a 96 well replicator. The replicator is flame sterilized with alcohol, rinsed with sterile water, and blotted on sterile paper towels between each transfer.

The results of % control of plant fungi at a certain concentration of compounds of this invention are shown in Tables IVa and IVb.

TABLE IIIa

BIOCIDES SECONDARY MIC TEST DATA IN PPM
These compounds were tested in M9G (minimal, salts media with glucose)

| Cpd # | (G−) PSFL | (G−) PSAE | (G−) ECOL | (G+) SAUR | (F) ANIG | (F) APUL |
|---|---|---|---|---|---|---|
| 1 | 50 | 100 | >100 | 100 | 2 | <0.8 |
| 1 | 125 | 16 | 125 | 16 | 1 | 1 |
| 1 | 32 | 63 | 32 | 8 | <4 | <4 |
| 2 | 50 | >100 | >100 | 50 | 3 | 3 |
| 3 | >100 | >100 | >100 | 25 | 3 | <0.8 |
| 4 | >10 | >100 | >100 | 25 | 3 | 3 |
| 5 | >100 | >100 | >100 | 63 | 25 | <0.8 |
| 6 | >100 | 100 | >100 | >100 | 25 | 32 |
| 6 | 500 | 500 | 500 | 64 | <4 | <4 |
| 7 | 13 | 100 | 100 | >100 | 3 | 2 |
| 7 | 125 | 125 | 64 | 500 | <0.8 | <0.8 |
| 8 | 125 | 125 | 64 | 500 | <4 | <4 |
| 8 | 25 | >100 | >100 | >100 | 3 | 2 |
| 9 | 25 | 125 | 64 | 500 | <4 | <4 |
| 10 | >100 | 100 | >100 | >100 | 3 | 6.3 |
| 11 | >100 | >100 | >100 | >100 | 6.3 | 3 |
| 22 | 100 | 100 | 100 | 100 | <0.8 | <0.8 |
| 23 | 63 | 32 | 16 | 63 | <4 | <4 |
| 23 | 16 | 250 | 125 | 32 | <4 | <4 |
| 24 | 63 | 32 | 32 | 125 | <4 | <4 |
| 24 | 32 | 125 | 63 | 63 | <4 | <4 |

TABLE IIIb

BIOCIDES SECONDARY MIC TEST DATA IN PPM
These compounds were tested in trypticase soy broth (complex media)

| Cpd # | (G−) PSFL | (G−) PSAE | (G−) ECOL | (G+) SAUR | (F) ANIG | (F) APUL |
|---|---|---|---|---|---|---|
| 28 | 63 | 63 | 63 | 63 | 2 | 4 |
| 29 | 32 | 125 | 125 | 32 | 0.50 | . |
| 30 | >250 | >250 | >250 | >250 | 0.12 | . |
| 31 | 32 | 63 | 250 | 32 | 2 | 4 |
| 32 | 32 | 63 | 63 | 63 | 2 | 8 |
| 34 | 63 | 125 | >250 | 250 | <0.12 | 8 |
| 35 | 63 | 125 | 125 | 63 | 2 | 4 |

TABLE IIIc

BIOCIDES SECONDARY MIC TEST DATA IN PPM
These compounds were tested in M9G (minimal salts media with glucose)

| Cpd # | (G−) PSFL | (G−) PSAE | (G−) ECOL | (G+) SAUR | (F) ANIG | (F) APUL |
|---|---|---|---|---|---|---|
| 12 | 50 | 50 | 50 | 50 | 6 | <0.8 |
| 13 | 50 | 50 | 100 | 50 | <0.8 | <0.8 |
| 14 | 100 | 50 | >100 | 100 | 6 | <0.8 |
| 15 | >100 | >100 | >100 | >100 | 6 | 1.6 |

TABLE IIIc-continued

BIOCIDES SECONDARY MIC TEST DATA IN PPM
These compounds were tested in M9G (minimal salts media with glucose)

| Cpd # | (G−) PSFL | (G−) PSAE | (G−) ECOL | (G+) SAUR | (F) ANIG | (F) APUL |
|---|---|---|---|---|---|---|
| 16 | >100 | >100 | >100 | 6 | 13 | <0.8 |
| 17 | 100 | 100 | 100 | 100 | <0.8 | <0.8 |
| 18 | 100 | 100 | 100 | >100 | <0.8 | <0.8 |
| 19 | 50 | 50 | 100 | 100 | <0.8 | <0.8 |
| 20 | 100 | 100 | 100 | 100 | <0.8 | <0.8 |
| 21 | 100 | 100 | 100 | >100 | <0.8 | 1.6 |
| 25 | 125 | 63 | 63 | 125 | <4 | <4 |
| 25 | 32 | 250 | 63 | 32 | <4 | <4 |
| 26 | 125 | 63 | 63 | 125 | <4 | <4 |
| 26 | 32 | 250 | 63 | 32 | 16 | 8 |
| 26 | 32 | 125 | 32 | 8 | <4 | 8 |
| 26 | 32 | 125 | 32 | 8 | <4 | 8 |
| 27 | 125 | 250 | 250 | 125 | <4 | 8 |

TABLE IVa

IN-VITRO PLANT FUNGICIDE TEST RESULTS
% Control at 25 ppm

| Compd # | BOC | FUS | HEL | PHY | PIR | PYU | RHI | SEP | XAN |
|---|---|---|---|---|---|---|---|---|---|
| 1 | 100 | 100 | 100 | 100 | 100 | 100 | 100 | 100 | 0 |
| 2 | 100 | 100 | 100 | 100 | 100 | 100 | 100 | 100 | 0 |
| 3 | 0* | 100 | 100 | 100 | 100 | 100 | 100 | 100 | 0 |
| 4 | 0* | 95 | 0* | 100 | 100 | 100 | 100 | 100 | 0 |
| 4 | 75 | 100 | 75 | 100 | 100 | 100 | 100 | 100 | 0 |
| 5 | 0* | 95 | 0 | 50 | 100 | 0 | 100 | 75 | 0 |
| 5 | 50 | 95 | 75 | 50 | 100 | 0 | 100 | 90 | 0 |
| 6 | 0 | 100 | 100 | 100 | 100 | 100 | 100 | 100 | 0 |
| 7 | 100 | 100 | 100 | 100 | 100 | 100 | 100 | 100 | 0 |
| 8 | 100 | 100 | 100 | 100 | 100 | 100 | 100 | 100 | 0 |
| 9 | 100 | 100 | 100 | 100 | 100 | 100 | 100 | 100 | 0 |
| 10 | 0* | 100 | 50 | 100 | 100 | 100 | 100 | 100 | 0 |
| 11 | 0 | 100 | 95 | 100 | 100 | 100 | 100 | 100 | 0 |
| 12 | 0 | 0* | 0* | 100 | 100 | 100 | 100 | 95 | 0 |
| 13 | 50 | 100 | 100 | 100 | 100 | 100 | 100 | 100 | 0 |
| 14 | 0 | 100 | 50 | 75 | 100 | 0 | 90 | 0 | 0 |
| 15 | 0 | 100 | 0* | 100 | 100 | 100 | 100 | 100 | 0 |
| 16 | 0 | 0* | 0* | 0 | 100 | 100 | 100 | 100 | 0 |
| 17 | 75 | 100 | 50 | 100 | 100 | 100 | 100 | 75 | 0 |
| 18 | 50 | 100 | 100 | 100 | 100 | 100 | 100 | 100 | 0 |
| 19 | 00 | 100 | 100 | 100 | 100 | 100 | 100 | 100 | 0 |
| 20 | 0 | 100 | 100 | 100 | 100 | 100 | 100 | 100 | 0 |
| 21 | 0 | 0* | 0* | 100 | 100 | 100 | 100 | 100 | 0 |
| 22 | 100 | 100 | 100 | 100 | 100 | 100 | 100 | 100 | 0 |
| 23 | 100 | 100 | 100 | . | 100 | 100 | 100 | 100 | 0 |
| 24 | 0 | 75 | 100 | . | 100 | 100 | 100 | 100 | 0 |
| 27 | 75 | 100 | 100 | . | 0 | 100 | 100 | 100 | 0 |
| 28 | 100 | 100 | 100 | 100 | 100 | 100 | 100 | 100 | 50 |
| 29 | 100 | 100 | 100 | 100 | 100 | 100 | 100 | 100 | 0 |
| 30 | 100 | 100 | 100 | 100 | 100 | 100 | 90 | 75 | 0 |

*Phytotoxic

TABLE IVb

IN-VITRO PLANT FUNGICIDE DATA
% Control at (ppm) indicated

| Cpd # | ALT | BOC | CER | COL | FUS | HEL | MON | PHY | PIR | PSH | PYU | RHI | SEP | UST | XAN |
|---|---|---|---|---|---|---|---|---|---|---|---|---|---|---|---|
| 1 | | | | | | | | | | | | | | | |
| (25) | 100 | 100 | 100 | 95 | 100 | 100 | 100 | 100 | 100 | 100 | 100 | 100 | 100 | 100 | 0 |
| (12) | 100 | 100 | 100 | 95 | 100 | 100 | 100 | 100 | 100 | 100 | 100 | 100 | 100 | 100 | 0 |
| (6) | 50 | 0 | 100 | 0* | 100 | 75 | 100 | 100 | 100 | 100 | 100 | 100 | 100 | 100 | 0 |
| (3) | 50 | 0 | 95 | 0 | 75 | 50 | 95 | 100 | 100 | 100 | 100 | 0* | 100 | 0 | 0 |
| (1.5) | 0 | 0 | 0 | 0 | 0* | 0* | 75 | 50 | 50 | 100 | 100 | 0 | 100 | 0 | 0 |
| (.8) | 0 | 0 | 0 | 0 | 0* | 0* | 0 | 0 | 0 | 75 | 0 | 100 | 0 | 50 | 0 |
| (.4) | 0 | 0 | 0 | 0 | 0* | 0 | 0 | 0 | 0 | 0 | 0 | 75 | 0 | 0 | 0 |
| (.2) | 0 | 0 | 0 | 0 | 0* | 0 | 0 | 0 | 0 | 0 | 0 | 0 | 0 | 0 | 0 |
| 19 | | | | | | | | | | | | | | | |
| (25) | 100 | 90 | 100 | 0 | 0* | 100 | 100 | 100 | 100 | 100 | 100 | 100 | 100 | 100 | 0 |
| (12) | 100 | 50 | 50 | 0 | 0 | 0 | 100 | 100 | 90 | 100 | 100 | 50 | 100 | 100 | 0 |
| (6) | 75 | 0 | 50 | 0 | 0 | 0 | 100 | 0 | 0 | 100 | 0 | 0 | 100 | 100 | 0 |
| (3) | 50 | 0 | 0 | 0 | 0 | 0 | 75 | 0 | 0 | 75 | 0 | 0 | 95 | 0 | 0 |
| (1.5) | 0 | 0 | 0 | 0 | 0 | 0 | 50 | 0 | 0 | 50 | 0 | 0 | 50 | 0 | 0 |
| (.8) | 0 | 0 | 0 | 0 | 0 | 0 | 0 | 0 | 0 | 0 | 0 | 0 | 0 | 0 | 0 |
| (.4) | 0 | 0 | 0 | 0 | 0 | 0 | 0 | 0 | 0 | 0 | 0 | 0 | 0 | 0 | 0 |
| (.2) | 0 | 0 | 0 | 0 | 0 | 0 | 0 | 0 | 0 | 0 | 0 | 0 | 0 | 0 | 0 |
| 28 | | | | | | | | | | | | | | | |
| (25) | 100 | 100 | 100 | 50 | 100 | 100 | 100 | 100 | 100 | 100 | 100 | 100 | 100 | 100 | — |
| (12) | 100 | 50 | 100 | 0 | 100 | 100 | 100 | 100* | 100 | 100 | 100 | 100 | 50 | 100 | — |
| (6) | 75 | 0 | 100 | 0 | 100 | 100 | 100 | 100 | 100 | 100 | 100 | 0 | 100 | 100 | — |
| (3) | 0* | 0 | 0 | 0 | 0 | 75 | 95 | 100 | 50 | 100 | 95 | 100 | 0 | 100 | — |

TABLE IVb-continued

IN-VITRO PLANT FUNGICIDE DATA
% Control at (ppm) indicated

| Cpd # | ALT | BOC | CER | COL | FUS | HEL | MON | PHY | PIR | PSH | PYU | RHI | SEP | UST | XAN |
|---|---|---|---|---|---|---|---|---|---|---|---|---|---|---|---|
| (1.5) | 0* | 0 | 0 | 0 | 0 | 0* | 0 | 0 | 0 | 95 | 0 | 100 | 0 | 50 | — |
| (.8) | 0 | 0 | 0 | 0 | 0 | 0 | 0 | 0 | 0 | 0 | 0 | 0 | 0 | 0 | — |
| (.4) | 0 | 0 | 0 | 0 | 0 | 0 | 0 | 0 | 0 | 0 | 0 | 0 | 0 | 0 | — |
| (.2) | 0 | 0 | 0 | 0 | 0 | 0 | 0 | 0 | 0 | 0 | 0 | 0 | 0 | 0 | — |
| 30 | | | | | | | | | | | | | | | |
| (25) | 100 | 90 | 100 | 100 | 100 | 100 | 100 | 100 | 100 | 100 | 100 | 100 | 100 | 0 | |
| (12) | 100 | 0 | 100 | 100 | 100 | 100 | 100 | 100 | 100 | 100 | 100 | 100 | 100 | 0 | |
| (6) | 90 | 0 | 50 | 50 | 100 | 100 | 100 | 100 | 100 | 100 | 100 | 100 | 100 | 0 | |
| (3) | 50 | 0 | 0 | 0 | 100 | 50 | 100 | 100 | 100 | 100 | 100 | 50 | 100 | 0 | |
| (1.5) | 0 | 0 | 0 | 0 | 0 | 0* | 100 | 100 | 100 | 100 | 100 | 0 | 100 | 0 | |
| (.8) | 0 | 0 | 0 | 0 | 0 | 0* | 100 | 0 | 100 | 100 | 100 | 0 | 100 | 0 | |
| (.4) | 0 | 0 | 0 | 0 | 0 | 0 | 100 | 0 | 0 | 100 | 100 | 0 | 0 | 0 | |
| (.2) | 0 | 0 | 0 | 0 | 0 | 0 | 100 | 0 | 0 | 0 | 100 | 0 | 0 | 0 | |

TABLE V

BIOCIDES BROAD SPECTRUM SECONDARY TEST RESULTS AGAINST 7 FUNGI

| Cpd. # | PPM | ANIG | PFUN | CRES | APUL | GTRA | SSER | RRUB |
|---|---|---|---|---|---|---|---|---|
| 1 | 25 | 1 | 1 | 1 | 1 | 1 | 1 | 1 |
|   | 5 | 1 | 0 | 0 | 0 | 1 | 0 | 0 |
|   | 1 | 0 | 0 | 0 | 0 | 1 | 0 | 0 |
|   | 0.2 | 0 | 0 | 0 | 0 | 0 | 0 | 0 |
| 29 | 25 | 1 | 1 | 1 | 1 | 1 | 1 | 1 |
|   | 5 | 1 | 1 | 1 | 1 | 1 | 1 | 1 |
|   | 1 | 0 | 0 | 0 | 0 | 1 | 0 | 0 |
|   | 0.2 | 0 | 0 | 0 | 0 | 1 | 0 | 0 |

[1]Test was run on Mycophile agar, pH 5.0
1 = no growth
0 = growth of the indicated fungi at dose indicated in ppm.

TABLE VI

BIOCIDES SECONDARY TEST RESULTS AGAINST 8 FUNGI
(Tested on Mycophile Agar at pH 5.0 at indicated dose level)

| Cpd. # | PPM | ANIG | PFUN | CRES | APUL | CGLO | GTRA | SSER | RRUB |
|---|---|---|---|---|---|---|---|---|---|
| 28 | 25 | 1 | 1 | 1 | 1 | 1 | 1 | 1 | 1 |
|   | 2.5 | 0 | 0 | 0 | 0 | 0 | 0 | 0 | 0 |
|   | 1.0 | 0 | 0 | 0 | 0 | 0 | 0 | 0 | 0 |
|   | 0.2 | 0 | 0 | 0 | 0 | 0 | 0 | 0 | 0 |
| 29 | 25 | 1 | 1 | 1 | 1 | 1 | 1 | 1 | 1 |
|   | 2.5 | 1 | 1 | 0 | 0 | 0 | 1 | 0 | 0 |
|   | 1.0 | 1 | 0 | 0 | 0 | 0 | 1 | 0 | 0 |
|   | 0.2 | 0 | 0 | 0 | 0 | 0 | 0 | 0 | 0 |
| 30 | 25 | 1 | 1 | 1 | 1 | 1 | 1 | 1 | 1 |
|   | 2.5 | 0 | 0 | 0 | 0 | 1 | 1 | 1 | 0 |
|   | 1.0 | 0 | 0 | 0 | 0 | 0 | 0 | 0 | 0 |
|   | 0.2 | 0 | 0 | 0 | 0 | 0 | 0 | 0 | 0 |
| 31 | 25 | 1 | 1 | 1 | 1 | 1 | 1 | 1 | 1 |
|   | 2.5 | 1 | 1 | 0 | 0 | 1 | 1 | 0 | 0 |
|   | 1.0 | 0 | 0 | 0 | 0 | 0 | 0 | 0 | 0 |
|   | 0.2 | 0 | 0 | 0 | 0 | 0 | 0 | 0 | 0 |
| 32 | 25 | 1 | 1 | 1 | 1 | 1 | 1 | 1 | 1 |
|   | 2.5 | 0 | 0 | 0 | 0 | 0 | 0 | 0 | 0 |
|   | 1.0 | 0 | 0 | 0 | 0 | 0 | 0 | 0 | 0 |
|   | 0.2 | 0 | 0 | 0 | 0 | 0 | 0 | 0 | 0 |
| 34 | 25 | 1 | 1 | 1 | 1 | 1 | 1 | 1 | 1 |
|   | 2.5 | 1 | 1 | 0 | 0 | 1 | 1 | 0 | 0 |
|   | 1.0 | 1 | 0 | 0 | 0 | 1 | 1 | 0 | 0 |
|   | 0.2 | 0 | 0 | 0 | 0 | 0 | 0 | 0 | 0 |
| 35 | 25 | 1 | 1 | 1 | 1 | 1 | 1 | 1 | 1 |
|   | 2.1 | 1 | 1 | 0 | 0 | 1 | 1 | 0 | 1 |
|   | 1.0 | 1 | 0 | 0 | 0 | 1 | 1 | 0 | 0 |
|   | 0.2 | 0 | 0 | 0 | 0 | 0 | 0 | 0 | 0 |

TABLE VII

MIC TEST AGAINST THREE FUNGI
(Test was in Mycophile Broth, pH 5.0, serial dilutions with a starting concentration of 50 ppm, test was read after 8 days of incubation.)

| Cpd. # | ANIG | APUL | GTRA |
|---|---|---|---|
| 1 | 3.2 | 12.5 | 1.6 |
| 2 | 3.2 | 25 | 1.6 |

TABLE VII-continued

MIC TEST AGAINST THREE FUNGI
(Test was in Mycophile Broth, pH 5.0, serial dilutions with a starting concentration of 50 ppm, test was read after 8 days of incubation.)

| Cpd. # | ANIG | APUL | GTRA |
|---|---|---|---|
| 3 | 25 | 50 | 3.2 |
| 4 | 50 | 50 | 6.2 |
| 5 | >50 | >50 | 6.2 |
| 6 | 12.5 | 25 | 3.2 |
| 7 | 25 | 50 | 12.5 |
| 8 | 12.5 | 25 | 12.5 |
| 9 | 25 | 50 | 12.5 |
| 10 | 6.2 | 12.5 | 6.2 |
| 11 | 25 | 50 | 12.5 |
| 12 | 25 | >50 | 6.2 |
| 13 | 25 | 50 | 6.2 |
| 14 | 50 | >50 | 12.5 |
| 15 | >50 | >50 | 50 |
| 16 | >50 | >50 | 25 |
| 17 | 12.5 | 50 | 25 |
| 18 | 12.5 | 50 | 12.5 |
| 19 | 50 | 50 | 50 |
| 20 | 50 | 50 | 12.5 |
| 21 | 50 | >50 | 50 |
| 22 | 12.5 | 50 | 12.5 |
| 23 | 6.2 | 25 | 1.6 |
| 24 | 12.5 | 25 | 12.5 |
| 25 | 50 | >50 | 6.2 |
| 26 | 25 | 50 | 6.2 |
| 27 | 25 | 50 | 6.2 |
| 28 | 12.5 | 50 | 6.2 |
| 29 | 1.6 | 12.5 | 3.2 |
| 30 | 12.5 | 50 | 6.2 |
| 31 | 1.6 | 6.2 | 0.8 |
| 32 | 12.5 | 25 | 3.2 |
| 34 | 1.6 | 12.5 | 3.2 |
| 35 | 1.6 | 6.2 | 0.4 |

TABLE VIII

BIOCIDES MIC TEST AGAINST MIXED COOLING TOWER ALGAE

| Cpd. # | PPM |
|---|---|
| 28 | 6.2 |
| 29 | 6.2 |
| 30 | 6.2 |
| 31 | 6.2 |
| 32 | 6.2 |
| 34 | 12.5 |
| 35 | 6.2 |

TABLE IX

MICROORGANISMS USED IN THE BIOCIDES TESTS

| Name | GRAM | ATCC No. | Abbreviation used |
|---|---|---|---|
| BACTERIA | | | |
| 1. Proteus mirabilis | (−) | 9921 | PMIR |
| 2. Pseudomonas aeruginosa | (−) | 15442 | PSAE |
| 3. Streptomyces spp. | (+) | 19930 | STRP |
| 4. Staphylococcus aureus | (+) | 6538 | SAUR |
| 5. Escherichia coli | (−) | 11229 | ECOL |
| 6. Pseudomonas fluorescens | (−) | 948 | PSFL |
| 7. Serratia marescens | (−) | 60 | SMAR |
| 8. Enterobacter aerogens | (−) | 13048 | EEAE |
| 9. Bacillus subtilis | (+) | 6633 | BSUB |
| 10. Pseudomonas cepacia | (−) | 17765 | PSCP |
| 11. Salmonella choleraesuis | (−) | 10708 | SCHO |
| 12. Flavobacterium flavescens | (−) | 8315 | FFLA |
| FUNGI | | | |
| 1. Aspergillus niger | | 6275 | ANIG |
| 2. Penicillium funiculosum | | 11797 | PFUN |
| 3. Cladosporium resinae | | 52833 | CRES |
| 4. Aureobasidium pullulans | | 9348 | APUL |
| 5. Chaetomium globosum | | 6205 | CGLO |
| 6. Poria placenta | | 11538 | PPLA |
| 7. Gloeophyllum trabeum | | 11539 | GTRA |

TABLE IX-continued

MICROORGANISMS USED IN THE BIOCIDES TESTS

| Name | GRAM | ATCC No. | Abbreviation used |
|---|---|---|---|
| YEAST | | | |
| 8. Sacharomyces cerevisiae | | 560 | SSER |
| 9. Rhodotorula rubra | | 2503 | RRUB |

We claim:

1. Compounds of the formula

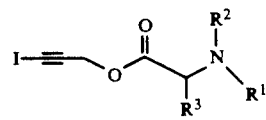

(I)

wherein $R^1$ is a radical which forms an amide, carbamate, enamine, or aminoacetal with the nitrogen to which it is attached or is selected from the group consisting of H, an amine protective group selected from the group consisting of amide, carbamate, imine, enamine, aminoacetal, alkyl, benzyl, sulfenyl, sulfonyl, and a moiety of the formula

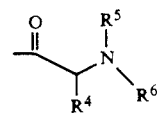

(II)

wherein
$R^2$, $R^5$, and $R^6$ are independently selected from H, and an amine protective group selected from the group consisting of amide, carbamate, imine, enamine, aminoacetal, alkyl, benzyl, sulfenyl, sulfonyl, or a radical which forms an amide, carbamate, enamine, or aminoocetal with the nitrogen to which it is attached $R^3$ and $R^4$ are independently selected from H, lower alkyl, aryl, arylalkyl, $CH_2OR$, $CH_2SR$ and $CH(CH_3)OR$;

R=H, propargyl, lower alkyl, arylalkyl or aryl; wherein $R^1$ and $R^2$ or $R^5$ and $R^6$ can be joined to form a ring; and wherein when $R^1$ and $R^2$ or $R^5$ and $R^6$ are both H, the compound is either in free base form or in salt form said compound is selected from the group consisting of N-t-butoxycarbonyl glycine iodopropargyl ester; N-t-butoxycarbonyl-L-alanine iodopropargyl ester; N-t-butoxycarbonyl-O-benzyl-L-serine iodopropargyl ester; N-t-butoxycarbonyl-S-benzyl-L-cysteine iodopropargyl ester; N-t-butoxycarbonyl-O-benzyl-L-threonine iodopropargyl ester; N-t-butoxycarbonyl-S-propargyl-L-cysteine iodopropargyl ester; glycine iodopropargyl ester trifluoroacetate; L-alanine iodopropargyl ester trifluoroacetate; O-benzyl-L-serine iodopropargyl ester trifluoroacetate; S-benzyl-L-cysteine iodopropargyl ester trifluoroacetate; O-benzyl-L-threonine iodopropargyl ester trifluoroacetate; N-t-butoxycarbonyl-L-alanylglycine iodopropargyl ester; N-t-butoxycarbonyl-L-alanyl-L-alanine iodopropargyl ester; N-t-butoxycarbonyl-L-alanyl-O-benzyl-L-serine iodopropargyl ester; N-t-butoxycarbonyl-L-alanyl-S-benzyl-L-cysteine iodopropargyl ester; N-t-butoxycarbonyl-L-alanyl-O-benzyl-L-threonine iodopropargyl ester; L-alanylglycine iodopropargyl ester trifluoroacetate; L-alanyl-L-alanine iodopropargyl ester trifluoroacetate; L-alanyl-O-benzyl-L-serine iodopropargyl ester trifluoroacetate; L-alanyl-S-benzyl-L-cysteine iodopropargyl ester trifluoroacetate; L-alanyl-O-benzyl-L-threonine iodopropargyl ester trifluoroacetate; L-alanine iodopropargyl ester; L-cysteine trifluoroacetate; N-t-butoxycarbonyl-D-alanine iodopropargyl ester; D-alanine iodopropargyl ester trifluoroacetate; N-t-butoxycarbonyl-D-alanyl-D-alanine iodopropargyl ester; N-t-butoxycarbonyl-D-alanyl-L-alanine iodopropargyl ester; N-t-butoxycarbonylglycyl-L-alanine iodopropargyl ester; N-acetylglycine iodopropargyl ester; N-benzoylglycine iodopropargyl ester; N-phthaloylglycine iodopropargyl ester; N-benzyloxycarbonylglycine iodopropargyl ester; N-formylglycine iodopropargyl ester; N-propionylglycine iodopropargyl ester; N-octanoylglycine iodopropargyl ester; N-sorboylglycine iodopropargyl ester.

2. Compound according to claim 1 wherein said compound is in salt form with a conjugate acid selected from the group consisting of hydrochloric, sulfuric, acetic, propionic, sorbic, trifluoroacetic, hydrobromic, and formic.

3. Compound according to claim 1 wherein $R^1$ and $R^2$ or $R^5$ and $R^6$ are joined to form a ring which is a cyclic derivative selected from the group consisting of phthalimido, diphenylmaleimido, and dithiasuccinimido.

* * * * *

UNITED STATES PATENT AND TRADEMARK OFFICE
CERTIFICATE OF CORRECTION

PATENT NO. : 5,252,745

DATED : October 12, 1993

INVENTOR(S) : Margaret M. Bowers-Daines and Barry C. Lange

It is certified that error appears in the above-indentified patent and that said Letters Patent is hereby corrected as shown below:

Column 3, line 65, Column 4, lines 1, 22 and 26, and Column 5, line 1 change "n-protected" to read -- N-protected --

Column 4, line 11 after "Alternatively, the" add --N-protected--

Column 11, line 35 change "N-sorboyl" to read -- N-sorboylglycine --

Column 11, line 41 change "Sorboyl" to read --N-sorboylglycine --

Column 11, line 50 change "sorboyl" to read --N-sorboylglycine --

Column 12, line 12 change "N-sorbogl" to read --N-sorboylglycine --

Signed and Sealed this

Tenth Day of January, 1995

Attest:

BRUCE LEHMAN

*Attesting Officer*     *Commissioner of Patents and Trademarks*